United States Patent
Harding et al.

(10) Patent No.: US 7,938,805 B2
(45) Date of Patent: May 10, 2011

(54) RADIALLY COMPRESSIBLE BLOOD CONTROL VALVE

(75) Inventors: Weston F. Harding, Lehi, UT (US); Austin Jason McKinnon, Herriman, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 71 days.

(21) Appl. No.: 12/123,259

(22) Filed: May 19, 2008

(65) Prior Publication Data
US 2009/0287154 A1    Nov. 19, 2009

(51) Int. Cl.
*A61M 5/178* (2006.01)
*F16K 15/00* (2006.01)

(52) U.S. Cl. .................... 604/167.04; 251/334

(58) Field of Classification Search ............ 604/167.04, 604/167.02, 167.03, 34, 246; 251/334
See application file for complete search history.

(56) References Cited

U.S. PATENT DOCUMENTS

| | | | |
|---|---|---|---|
| 3,811,440 A | 5/1974 | Moorehead et al. | |
| 3,856,010 A | 12/1974 | Moorehead et al. | |
| 3,895,632 A | 7/1975 | Plowiecki | |
| 3,977,400 A | 8/1976 | Moorehead | |
| 4,387,879 A | 6/1983 | Tauschinski | |
| 4,842,591 A | 6/1989 | Luther | |
| 4,874,377 A | 10/1989 | Newgard et al. | |
| 4,917,668 A | 4/1990 | Haindl | |
| 5,009,391 A | 4/1991 | Steigerwald | |
| 5,061,253 A | 10/1991 | Yoshida | |
| 5,071,411 A | 12/1991 | Hillstead | |
| 5,085,645 A | 2/1992 | Purdy et al. | |
| 5,098,394 A | 3/1992 | Luther | |
| 5,108,380 A | 4/1992 | Herlitze et al. | |
| 5,380,305 A | 1/1995 | Ghouri | |
| 5,429,616 A | 7/1995 | Schaffer | |
| 5,456,675 A | 10/1995 | Wolbring et al. | |
| 5,514,114 A | 5/1996 | Soto-Tolosa et al. | |
| 5,549,651 A * | 8/1996 | Lynn .......................... | 604/537 |
| 5,613,663 A | 3/1997 | Schmidt et al. | |
| 5,749,857 A | 5/1998 | Cuppy | |
| 5,782,816 A | 7/1998 | Werschmidt et al. | |
| 5,817,069 A | 10/1998 | Arnett | |
| 5,954,698 A | 9/1999 | Pike | |
| 5,967,490 A | 10/1999 | Pike | |
| 6,595,981 B2 | 7/2003 | Huet | |

(Continued)

FOREIGN PATENT DOCUMENTS

| | | |
|---|---|---|
| EP | 1 415 678 A1 | 5/2004 |
| WO | 2007/050788 A2 | 5/2007 |

(Continued)

*Primary Examiner* — Nicholas D Lucchesi
*Assistant Examiner* — Brooke M Matney
(74) *Attorney, Agent, or Firm* — Craig Metcalf; Mony Ghose; Kirton & McConkie

(57) ABSTRACT

An apparatus to control blood flow through an intravenous catheter in accordance with the present invention may include an intravenous catheter adapter and a blood control valve. The blood control valve may be retained within a hollow interior region of the intravenous catheter adapter, and may include a resilient outer shell and an inner valve portion extending inwardly therefrom. The inner valve portion may include a slit configured to open, coin-purse style, upon radially compressing the resilient outer shell. In some embodiments, a compression feature may be integrated into the intravenous catheter adapter to radially compress the resilient outer shell. A Luer device, for example, may be inserted into the intravenous catheter adapter to translate the blood control valve to a position substantially corresponding to the compression feature, thereby actuating the compression feature to open the slit.

20 Claims, 10 Drawing Sheets

U.S. PATENT DOCUMENTS

| | | |
|---|---|---|
| 6,699,221 B2 | 3/2004 | Vaillancourt |
| 7,008,404 B2 | 3/2006 | Nakajima |
| 2004/0044313 A1 | 3/2004 | Nakajima |
| 2004/0158208 A1* | 8/2004 | Hiejima .................. 604/167.04 |
| 2004/0167474 A1 | 8/2004 | Meng et al. |
| 2006/0155245 A1 | 7/2006 | Woehr |
| 2008/0108944 A1 | 5/2008 | Woehr et al. |

* cited by examiner

RADIALLY COMPRESSIBLE BLOOD CONTROL VALVE

BACKGROUND

The insertion of an intravenous catheter into a patient's bloodstream is one of the most commonly performed procedures in health care environments today. Such catheters are widely used to infuse fluids, such as saline solution, various medicaments, and/or total parenteral nutrition into a patient. They may also be used to withdraw blood from a patient, and/or monitor various parameters of the patient's vascular system.

Despite their prevalence and usefulness in health care environments, procedures used for intravenous catheter insertion present significant risks to the health care workers that perform them. Particularly, health care workers are at an increased risk for contracting viral hepatitis, Human Immunodeficiency Virus ("HIV"), the virus that causes Autoimmune Deficiency Virus ("AIDS"), and other blood-borne infectious diseases. This risk is increased as intravenous catheter insertion requires disassembly of the introducer needle from the catheter adapter once the catheter is properly positioned within a patient's bloodstream. This process requires a high level of dexterity and physical manipulation, with an accompanying increased risk of exposure to blood and blood pathogens.

To introduce an IV catheter into a patient, an over-the-needle catheter may be mounted over a hollow-bore introducer needle having a sharp distal tip. The inner surface of the catheter may tightly engage the outer surface of the needle to prevent catheter peelback and facilitate insertion of the catheter into a blood vessel. The tip of the introducer needle may extend beyond the distal tip of the catheter to enable insertion of the catheter at a shallow angle through the patient's skin and into a blood vessel.

To verify proper placement of the needle and catheter in the blood vessel, the clinician may confirm the presence of "flashback" blood in a flashback chamber associated with the catheter and needle assembly. Once proper placement is initially confirmed, the clinician may then remove the needle from the catheter and apply pressure to the blood vessel to occlude the vessel, thereby controlling further blood flow into the catheter assembly. This technique, however, is imprecise and may result in blood from the blood vessel exiting the catheter tube through the catheter adapter, thereby compromising sterility of the fluid path and potentially exposing the health care worker to blood and blood pathogens.

The requirement to apply digital pressure to the blood vessel after insertion of the catheter also leaves the health care worker with only one hand available to manipulate the catheter insertion assembly as needed to remove the needle and connect the catheter adapter to the administration set. This requirement thus further increases the potential for human error resulting in blood exposure and injuries related thereto.

Finally, typical catheter insertion practice requires the catheter to be further advanced into the blood vessel upon withdrawing the needle therefrom. While blood control valves exist to reduce an incidence of blood flow beyond the open end of the catheter adapter, such valves tend to impair a health care worker's continued ability to verify proper positioning of the catheter, since blood flashback may only be observed upon initial placement. Accordingly, known blood control valves tend to increase a potential for catheter failure and procedure duplication.

From the foregoing discussion, it should be apparent that a need exists for an intravenous catheter blood control device capable of controlling blood flow to facilitate visibility of blood flashback throughout a catheter insertion procedure, while minimizing a risk of blood exposure from blood spills through the catheter adapter. Beneficially, such an intravenous catheter blood control device would enable simple and inexpensive manufacture, as well as simple and effective operation. Such an intravenous catheter blood control device is disclosed and claimed herein.

BRIEF SUMMARY

The present invention has been developed in response to the present state of the art, and in particular, in response to the problems and needs in the art that have not yet been met by currently available intravenous catheter blood control valves. Accordingly, the present invention has been developed to provide an intravenous catheter blood control valve that overcomes many or all of the above-discussed shortcomings in the art.

An apparatus to control blood flow through an intravenous catheter in accordance with embodiments of the present invention may include an intravenous catheter adapter and a blood control valve. The blood control valve may be retained within a hollow interior region of the intravenous catheter adapter.

The blood control valve may include a resilient outer shell and inner valve portion extending inwardly therefrom. The inner valve portion may include a slit configured to open upon radially compressing the resilient outer shell. Further, in some embodiments, the inner valve portion may be configured to receive a needle therethrough. The resilient outer shell and/or the inner valve portion may be formed of an elastomeric material, such as silicone rubber.

In certain embodiments, the intravenous catheter adapter and/or the blood control valve may include a retention feature to retain the blood control valve within the hollow interior region of the intravenous catheter adapter. Likewise, the intravenous catheter adapter and/or blood control valve may include a positioning feature to properly orient the blood control valve within the hollow interior region.

In one embodiment, the intravenous catheter adapter includes a compression feature to selectively radially compress the resilient outer shell to open the inner valve portion. The blood control valve may be oriented within the hollow interior region such that a Luer device inserted into the intravenous catheter adapter translates the blood control valve in a proximal direction. In some embodiments, the Luer device translates the blood control valve to a position substantially corresponding to the compression feature, thereby actuating the compression feature to radially compress the resilient outer shell.

A method to control blood flow through an intravenous catheter in accordance with embodiments of the present invention is also presented. The method may include providing a blood control valve having a resilient outer shell, and forming an inner valve portion extending inwardly from the resilient outer shell. The inner valve portion may include a slit configured to open upon radially compressing the resilient outer shell. The method may further include providing an intravenous catheter adapter having a hollow interior region therein, and positioning the blood control valve within the hollow interior region.

In some embodiments, a compression feature may be integrated into the hollow interior region of the intravenous catheter adapter to selectively radially compress the resilient outer shell. The blood control valve may be translated to a position substantially corresponding to the compression feature to actuate the compression feature. In one embodiment, the blood control valve may be oriented within the hollow interior region such that a Luer device inserted into a distal end of the intravenous catheter adapter translates the blood control valve to a position substantially corresponding to the compression feature.

A retention feature to retain the blood control valve within the hollow interior region may be integrated into the intravenous catheter adapter and/or blood control valve. Likewise, a positioning feature to properly orient the blood control valve within the hollow interior region may be integrated into either or both of the intravenous catheter adapter and blood control valve.

An intravenous catheter assembly to control fluid flow through an intravenous catheter in accordance with the present invention may include means for piercing a blood vessel to acquire intravenous access, and means for mediating fluid communication between the blood vessel and an external fluid source. The intravenous catheter assembly may further include means for controlling fluid flow through the means for mediating fluid communication. The means for controlling fluid flow may include resilient outer shell means and inner valve means extending inwardly therefrom. The inner valve means may include slit means configured to open upon radially compressing the resilient outer shell means.

The means for mediating fluid communication may include means for radially compressing the resilient outer shell means. In some embodiments, the means for radially compressing the resilient outer shell means may be actuated upon inserting a Luer device into the means for mediating fluid communication to translate the means for controlling fluid flow to a position substantially corresponding to the means for radially compressing the resilient outer shell means.

These and other features and advantages of the present invention may be incorporated into certain embodiments of the invention and will become more fully apparent from the following description and appended claims, or may be learned by the practice of the invention as set forth hereinafter. The present invention does not require that all the advantageous features and all the advantages described herein be incorporated into every embodiment of the invention.

BRIEF DESCRIPTION OF THE SEVERAL VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION

The illustrated embodiments of the present invention will be best understood by reference to the drawings, wherein like parts are designated by like numerals throughout. It will be readily understood that the components of the present invention, as generally described and illustrated in the Figures herein, may be arranged and designed in a wide variety of different configurations. Thus, the following more detailed description, as presented in the Figures, is not intended to limit the scope of the invention as claimed, but is merely representative of selected embodiments of the invention. The following description is intended only by way of example, and simply illustrates certain selected embodiments of devices, systems, and processes that are consistent with the invention as claimed herein.

As used in this specification, the term "needle" refers to any of various devices that may be used to pierce the skin to acquire intravenous access, such as a hypodermic needle, a hollow-bore needle, a surgical knife, and the like. The term "catheter adapter" refers to a medical device providing fluid communication and mechanical connection between an intravenous catheter and another vascular access device, such as a needle safety device, syringe, intravenous tubing, or the like. The term "Luer device" refers to a medical device that includes standard Luer taper dimensions, as set forth in the International Organization for Standardization ("ISO") 594 standards. These standardized taper dimensions enable one or more Luer devices to be interconnected by male and female interlocking features.

Figure 1:
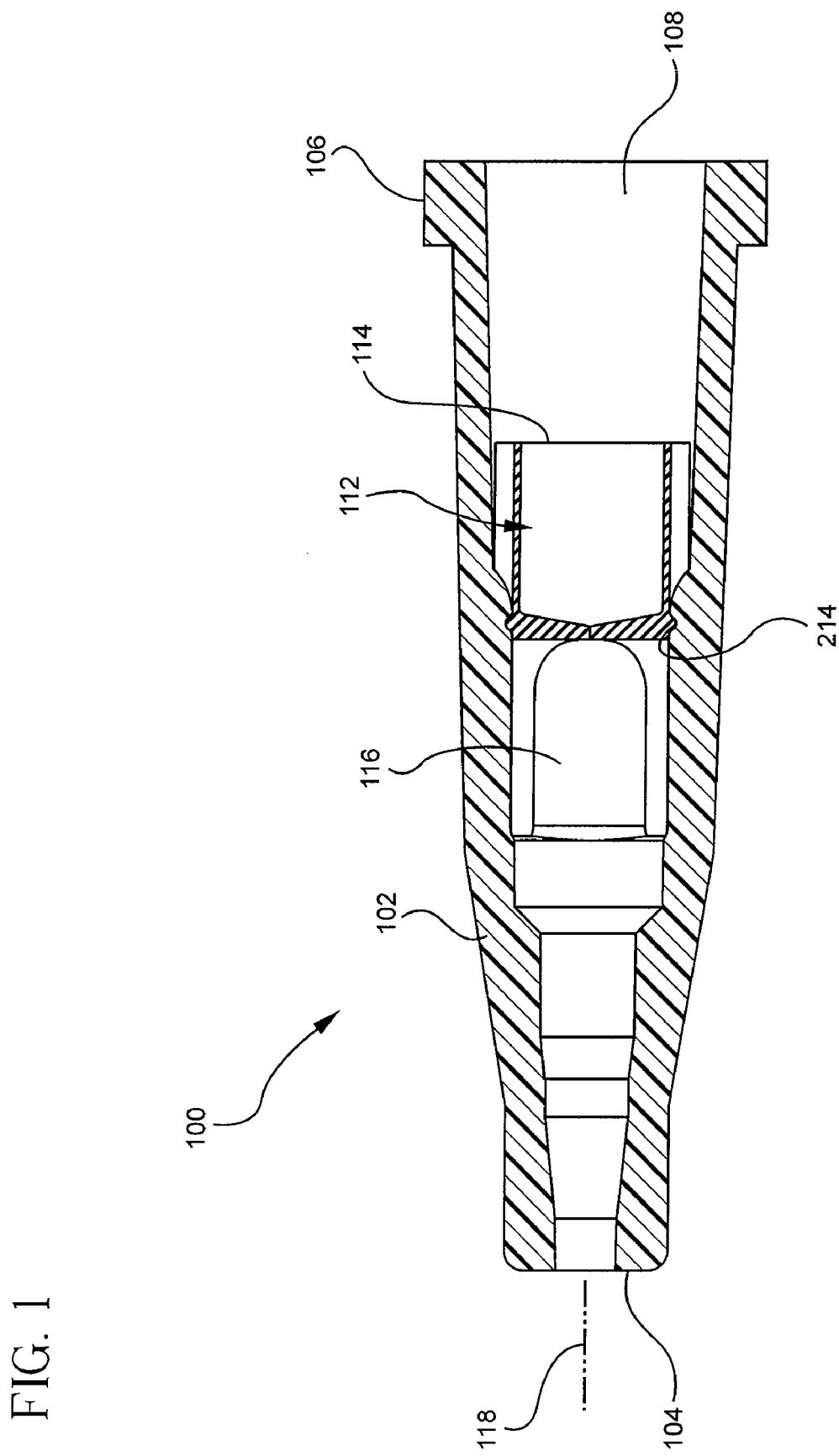
FIG. 1 is a cross-sectional view of an intravenous catheter assembly in accordance with certain embodiments of the present invention.

Referring now to FIG. 1, an intravenous catheter assembly 100 in accordance with the present invention may include a catheter adapter 102 and a blood control valve 112 residing therein. A catheter (not shown) may be coupled to or integrated with a proximal end 104 of the catheter adapter 102 to provide fluid communication between a blood vessel and an external fluid source.

The catheter adapter 102 may be longitudinally oriented around a longitudinal axis 118, and may include the proximal end 104, a distal end 106, and a hollow interior region 108 extending therebetween. An outer surface of the catheter adapter 102 may be substantially cylindrical and molded along the longitudinal axis 118 to provide a secure, comfortable grip. In some embodiments, for example, the catheter adapter 102 may include grooves, ridges or an otherwise textured outer surface to facilitate a secure grip. The hollow interior region 108 may include one or more compression features 116 coupled to or integrated therein to compress the blood control valve 112, as discussed in more detail below.

The proximal and distal ends 104, 106 of the catheter adapter 102 may be configured to receive a needle (not shown) therethrough along the longitudinal axis 118. In some embodiments, the proximal and distal ends 104, 106 of the catheter adapter 102 may include substantially smooth inner surfaces to facilitate manipulation of the needle.

The needle may be advanced through the catheter adapter 102 and attached catheter to facilitate an intravenous catheterization procedure. Specifically, the needle may be introduced through the proximal end 104 of the catheter adapter 102 and extend through the hollow interior region 108 to exit the distal end 106 thereof. The needle may then be guided through the attached catheter. The needle tip may protrude past the end of the catheter, enabling it to pierce a patient's skin to acquire intravenous access.

The blood control valve 112 may also be formed about the longitudinal axis 118. In some embodiments, for example, the blood control valve 112 may include a substantially cylindrical outer shell (not shown) having an inner valve portion (not shown) extending thereacross, as discussed in more detail with reference to FIG. 2 below. The blood control valve 112 may include an outside diameter at least slightly less than an inside diameter of the catheter adapter 102 to facilitate situating the blood control valve 112 within the hollow interior region 108. In some embodiments, the blood control valve 112 may be oriented within the hollow interior region 108 such that a distal edge 114 thereof may be accessed within the catheter adapter 102 by, for example, inserting a Luer device into the distal end 106.

Figure 2:
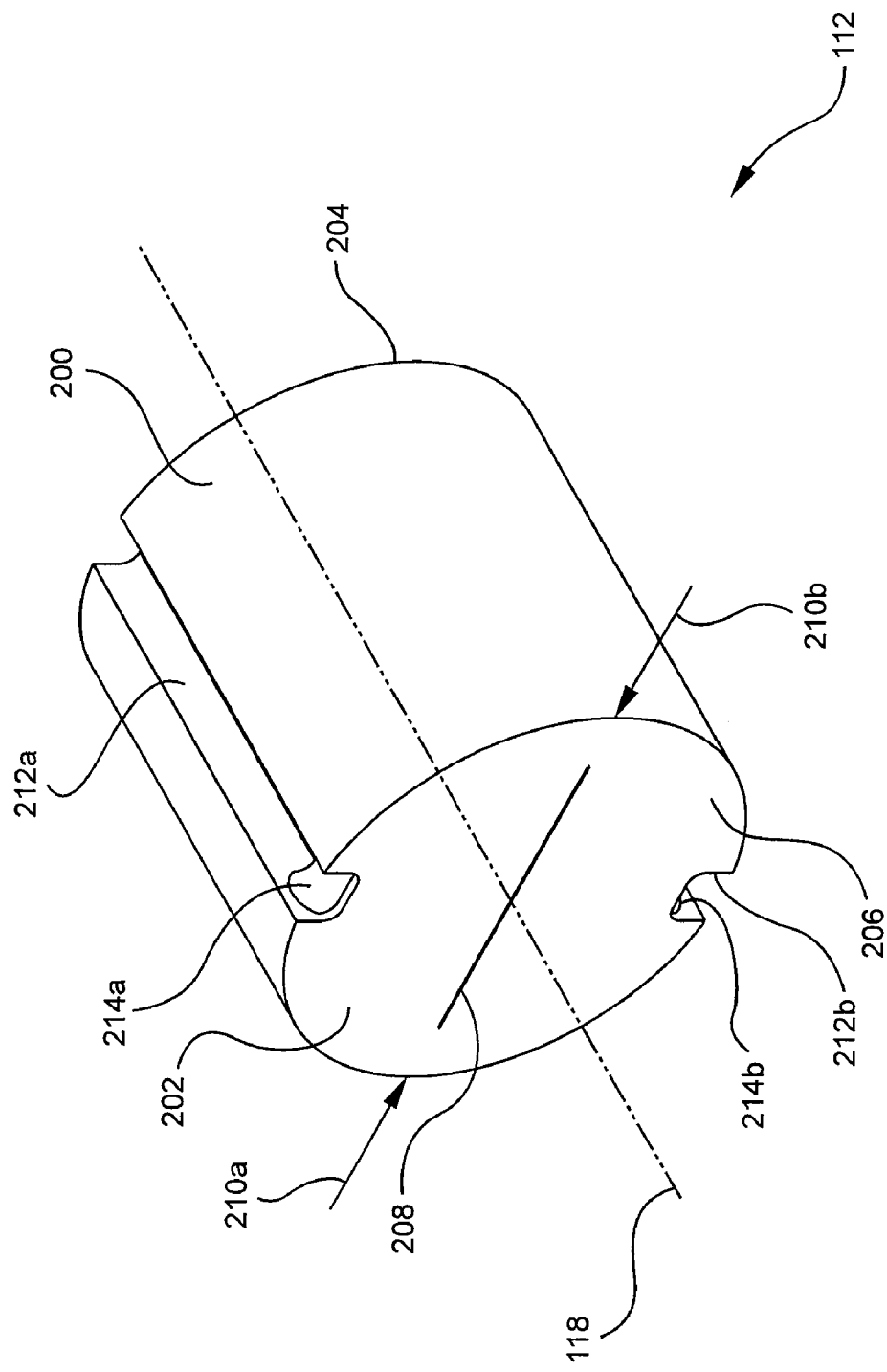
FIG. 2 is a perspective view of one embodiment of a blood control valve in accordance with the invention.
Figure 3:
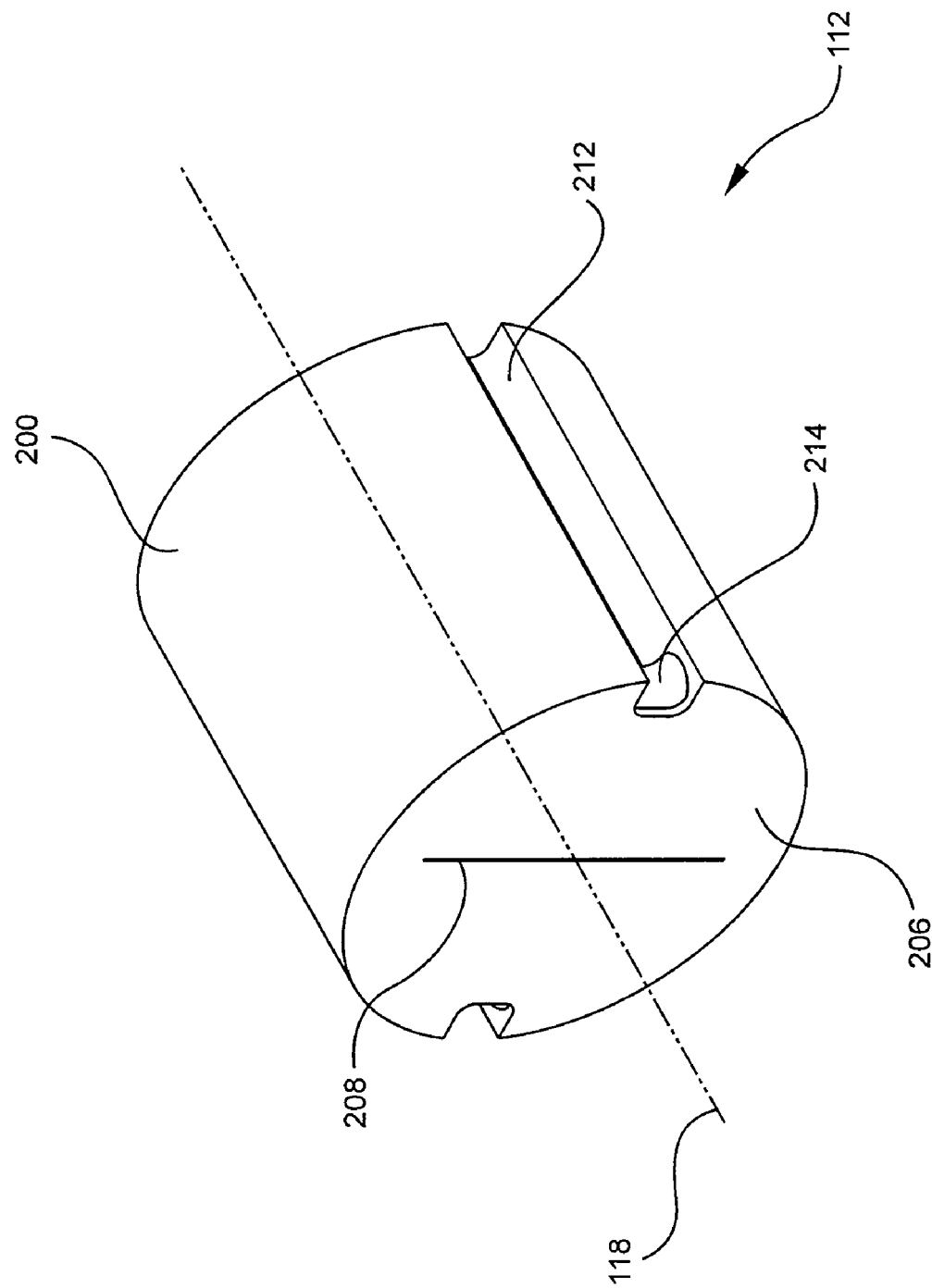
FIG. 3 is an alternate perspective view of a blood control valve having retention and positioning features integrated therein.

Referring now to FIGS. 2 and 3, the blood control valve 112 may be positioned within the catheter adapter 102 at a position to mediate fluid flow between the catheter and an external fluid source (not shown). The blood control valve 112 may include, for example, an elastomeric or resilient material such as silicone rubber, or any other suitable material known to those in the art.

The blood control valve 112 may include a substantially cylindrical resilient outer shell 200 oriented about the longitudinal axis 118. An inner valve portion 202 may extend inwardly from the outer shell 200 in a plane perpendicular to the longitudinal axis 118. In one embodiment, the inner valve portion 202 includes a membrane extending across a proximal end 202 of a substantially cylindrical outer shell 200. In other embodiments, the inner valve portion 202 may extend across the outer shell 200 at its distal end 204, or at any intermediary position known to those in the art.

A slit 208 may be disposed within the inner valve portion 202. The slit 208 may be oriented in any direction known to those in the art. In certain embodiments, the slit 208 may be positioned to substantially bisect the inner valve portion 206. In any case, the slit 208 may be configured to open upon radially compressing the outer shell 200, as discussed in more detail below.

The slit 208 may further accommodate an introducer needle advanced through the catheter adapter 102 and attached catheter to facilitate an intravenous catheterization process. The needle may be guided through the slit 208, thereby deforming the slit 208 as needed to permit the needle to extend beyond the blood control valve 112 into the proximal end 104 of the catheter adapter 102 and attached catheter.

The needle may be gradually retracted through the catheter and catheter adapter 102 once the catheter is properly positioned within a blood vessel. In some embodiments, the needle and blood control valve 112 may cooperate to enable continued visibility of blood flashback throughout such an intravenous catheterization procedure. This may provide continued confirmation that the catheter is properly positioned within the blood vessel.

For example, a flashback chamber (not shown) attached to a distal end of the needle may enable a health care worker to visualize blood flashback within the flashback chamber upon piercing a blood vessel with the needle. The catheter may then be further advanced into the blood vessel. The needle may be gradually retracted from within the catheter, thereby releasing a seal between the needle and catheter and creating annular space between the proximal end of the catheter and the needle tip. Blood flashback may gradually fill this annular space, providing continued evidence of proper positioning of the catheter within the blood vessel.

Finally, the catheter may be advanced within the blood vessel until the proximal end 104 of the catheter adapter 102 reaches the patient's skin. The needle may then be retracted such that the needle tip exits the catheter, the blood control valve 112, and finally the distal end 106 of the catheter adapter 102. The resiliency of the inner valve portion 206 of the blood control valve 112 may cause the slit 208 to substantially close following retraction of the needle tip therefrom.

While this automatic closure effectively prevents a free flow of blood into the catheter adapter 102 without requiring digital occlusion of the blood vessel, the blood control valve 112 continues to permit controlled, visible fluid leakage past the slit 208 and into a distal portion of the catheter adapter 102. Indeed, in some embodiments, the slit 208 may remain at least slightly open, even in the absence of any application of force. In other embodiments, small channels may be integrated into the blood control valve 112 or hollow interior region 108 to enable a metered flow of blood therethrough. This feature of the present invention may enable final confirmation that the catheter is properly positioned within the blood vessel.

Radially compressing the outer shell 200 in the plane perpendicular to the longitudinal axis 118 and at a position substantially corresponding to the slit 208 may cause the ends 224a, 224b of the slit 208 to be brought closer together. Such compression may cause the slit 208 to open, coin-purse style. In some embodiments, opposite radial forces 210a, 210b may be applied to the outer shell 200 proximate the inner valve portion 206. The uncompressed portions of the outer shell 200 may be substantially unrestricted to allow the slit 208 to open, thereby providing a fluid path between the blood vessel and the external fluid source. Radial compression in this manner may be achieved by, for example, translating the blood control valve 112 within the hollow interior region 108 to a position corresponding to one or more compression features 116 integrated therein. This process is discussed in more detail with reference to FIGS. 7, 8, and 9 below.

As shown in FIGS. 2 and 3, some embodiments of a blood control valve 112 in accordance with the present invention may incorporate one or more positioning features 212a, 212b to properly orient the blood control valve 112 within the hollow interior region 108. Such positioning features 212a, 212b may further maintain proper positioning of the blood control valve 112 within the hollow interior region 108 during translation of the blood control valve 112 therein.

In one embodiment, for example, positioning features 212a, 212b may include grooves or slots integrated into the outer shell 200 corresponding to guide ribs (not shown) formed within the hollow interior region 108. The grooves may be aligned with the guide ribs upon situating the blood control valve 112 within the catheter adapter 102. The grooves and guide ribs may then cooperate to maintain proper orientation of the blood control valve 112 within the catheter adapter 102, even where the blood control valve 112 is translated within the hollow interior region 108 of the catheter adapter 102.

In certain embodiments, the blood control valve 112 and/or catheter adapter 102 may further include one or more retention features 214a, 214b to retain the blood control valve 112 within the catheter adapter 102. Such retention features 214a, 214b may prevent inadvertent or intentional disassembly of the intravenous catheter assembly 100 to remove the blood control valve 112. Retention features 214a, 214b may include, for example, indentations, notches, hooks, projections, bulges, protuberances, or other features integrated into the outer shell 200. Retention features 214a, 214b may further include mating features integrated into the catheter adapter 102 that are configured to mate with the retention features 214a, 214b integrated into the outer shell 200, as discussed in more detail below.

Figure 4:
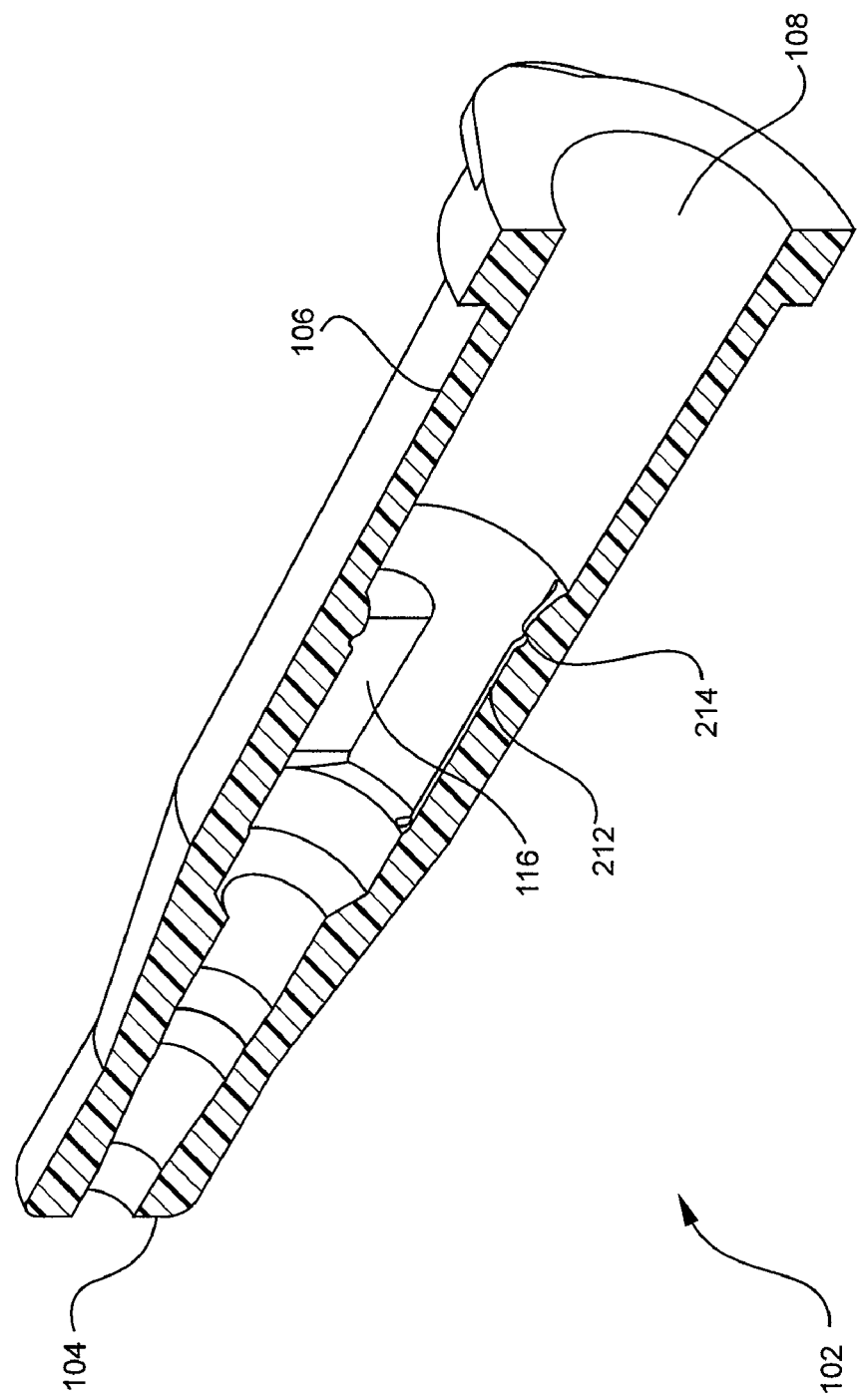
FIG. 4 is a cut-away perspective view of one embodiment of an intravenous catheter adapter having a compression feature integrated therein.

Referring now to FIG. 4, a catheter adapter 102 in accordance with the present invention may include one or more compression features 116 molded or attached therein to compress the blood control valve 112, as discussed above with reference to FIGS. 2 and 3. Compression features 116 may be integrated into the catheter adapter 102 at or near a proximal end 104 thereof, and may include, for example, opposing walls, flats, protuberances, ridges, or any other feature known to those in the art to effectively apply radial compression forces to the outer shell 200 to open the slit 208.

In some embodiments, the blood control valve 112 may be selectively translated toward the proximal end 104 of the catheter adapter 102 such that the compression features 116 substantially contact the outer shell 200. In one embodiment, for example, a Luer device may be inserted into a distal end 106 of the catheter adapter 102 to translate the blood control valve 112 therein. In this embodiment, the blood control valve 112 may be initially positioned within the catheter adapter 102 such that insertion of the Luer device effectively translates the blood control valve 112 from a more distal position to a more proximal position. As previously discussed, the compression features 116 may be strategically positioned within a proximal portion of the catheter adapter 102 to reduce the diameter of the hollow interior region 108 as needed to radially compress the outer shell 200, causing the slit 208 to open.

Figure 5:
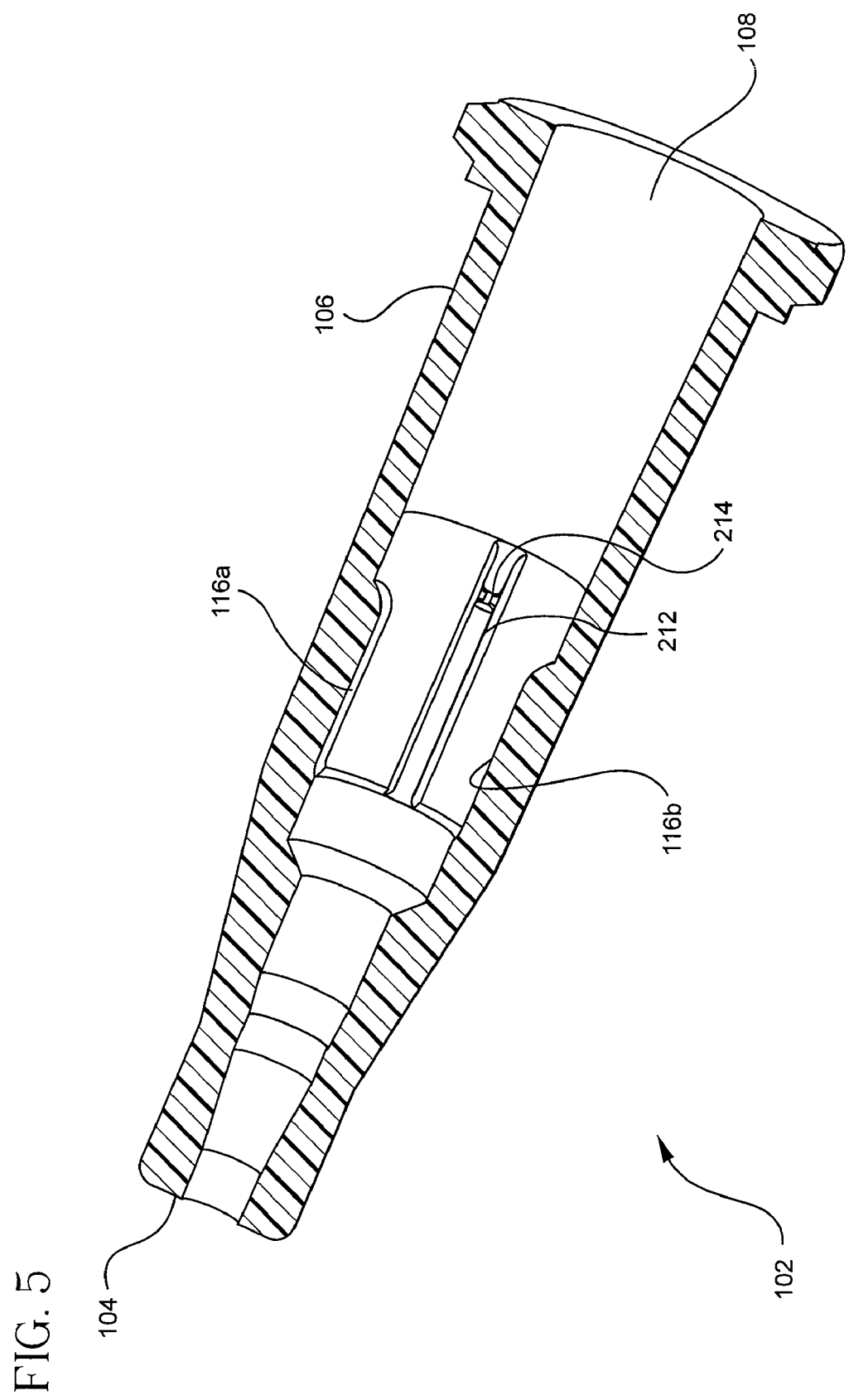
FIG. 5 is a cut-away perspective view of one embodiment of an intravenous catheter adapter having retention and positioning features integrated therein.
Figure 6A:
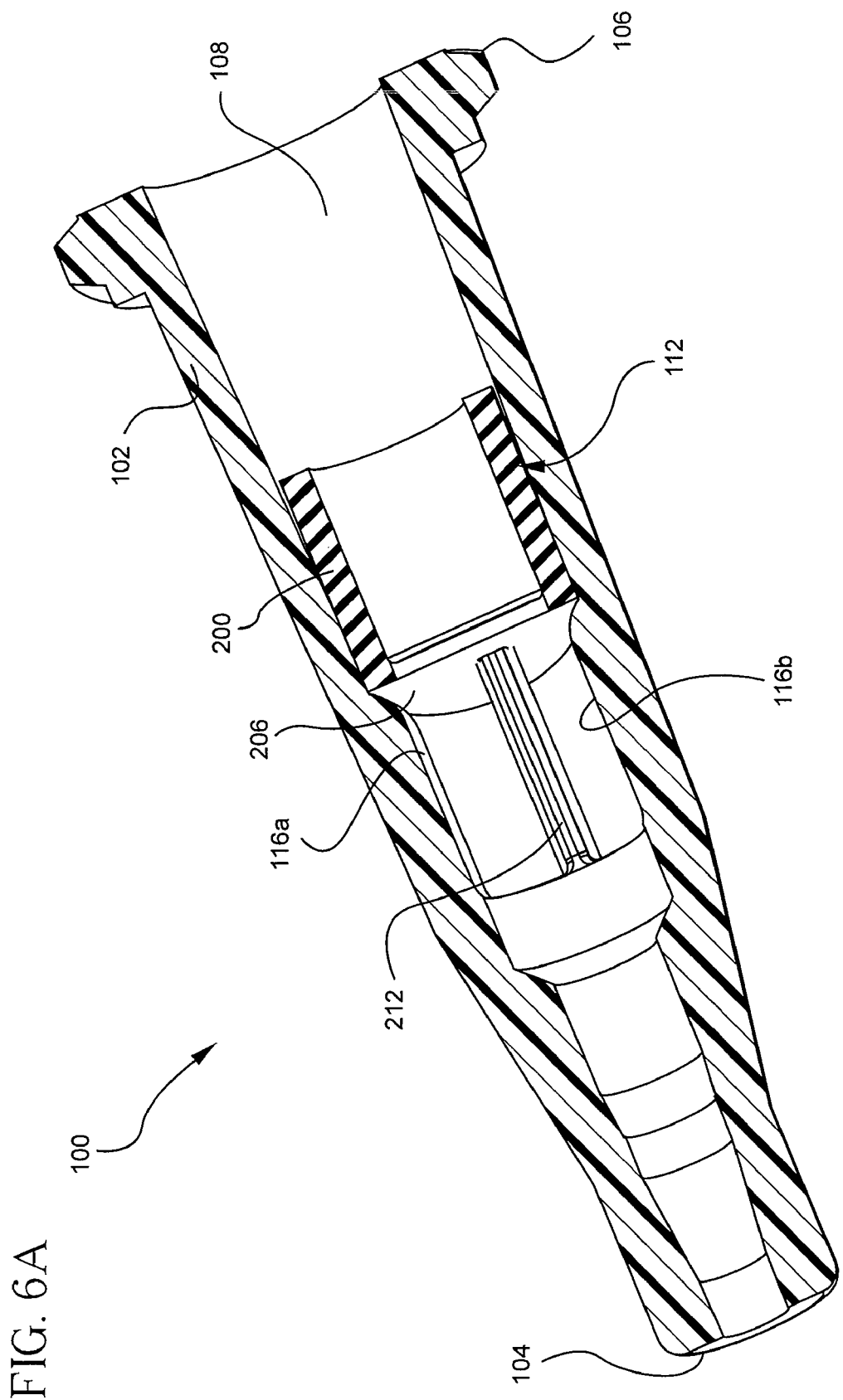
FIG. 6A is a perspective cross-sectional view of an intravenous catheter adapter and blood control valve having cooperating positioning features in accordance with certain embodiments of the present invention.
Figure 6B:
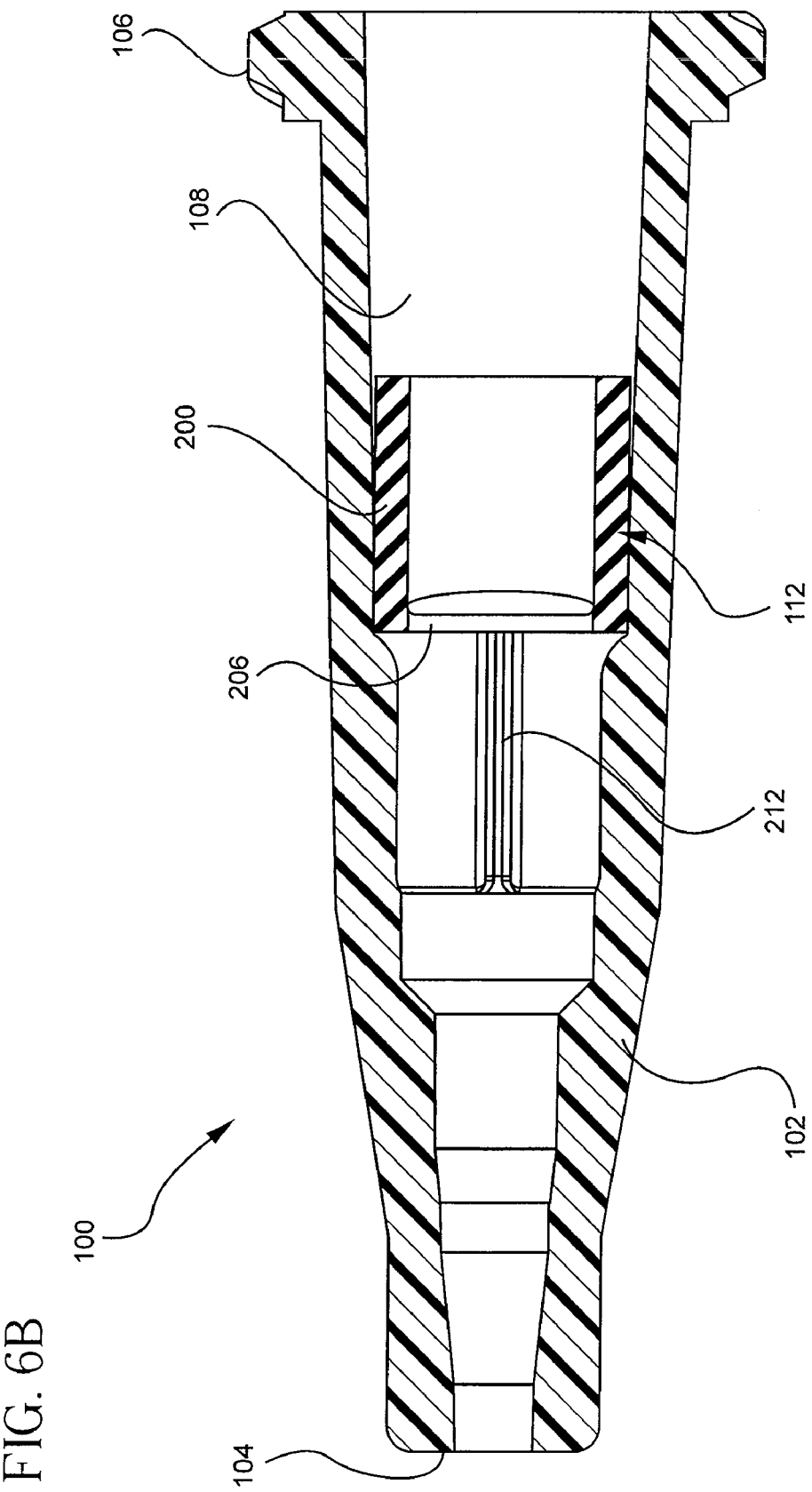
FIG. 6B is a cross-sectional view of the intravenous catheter adapter of FIG. 6A.

Referring now to FIGS. 5, 6A, and 6B, positioning features 212 may be integrated into or coupled to the hollow interior region 108 of the catheter adapter 102. Such positioning features 212 may cooperate with positioning features 212 integrated into the blood control valve 112 to properly orient the blood control valve 112 within the hollow interior region 108. Particularly, the positioning features 212 may cooperate to maintain proper orientation of the blood control valve 112 with respect to the compression features 116 upon translating the blood control valve 112. In this manner, translating the blood control valve 112 to contact the compression features 116 may cause the slit 208 to open.

Positioning features 212 formed within the hollow interior region 108 of the catheter adapter 102 may include, for example, ridges, guides, slots, grooves, ribs, or any other suitable positioning feature known to those in the art.

One or more retention features 214 may also be integrated into or coupled to the hollow interior region 108 of the catheter adapter 102. In one embodiment, a retention feature 214 may substantially correspond to a most distal end of a positioning feature 212 integrated therein. As with the positioning features 212, retention features 214 formed in the hollow interior region 108 of the catheter adapter 102 may mate with corresponding retention features 214 in the blood control valve 112 to prevent removal of the blood control valve 112 from the hollow interior region 108. Retention features 214 may include, for example, indentations, notches, hooks, projections, bulges, protuberances, or other features integrated into the hollow interior region 108 to mate with corresponding retention features 214 in the outer shell 200.

Figure 7:
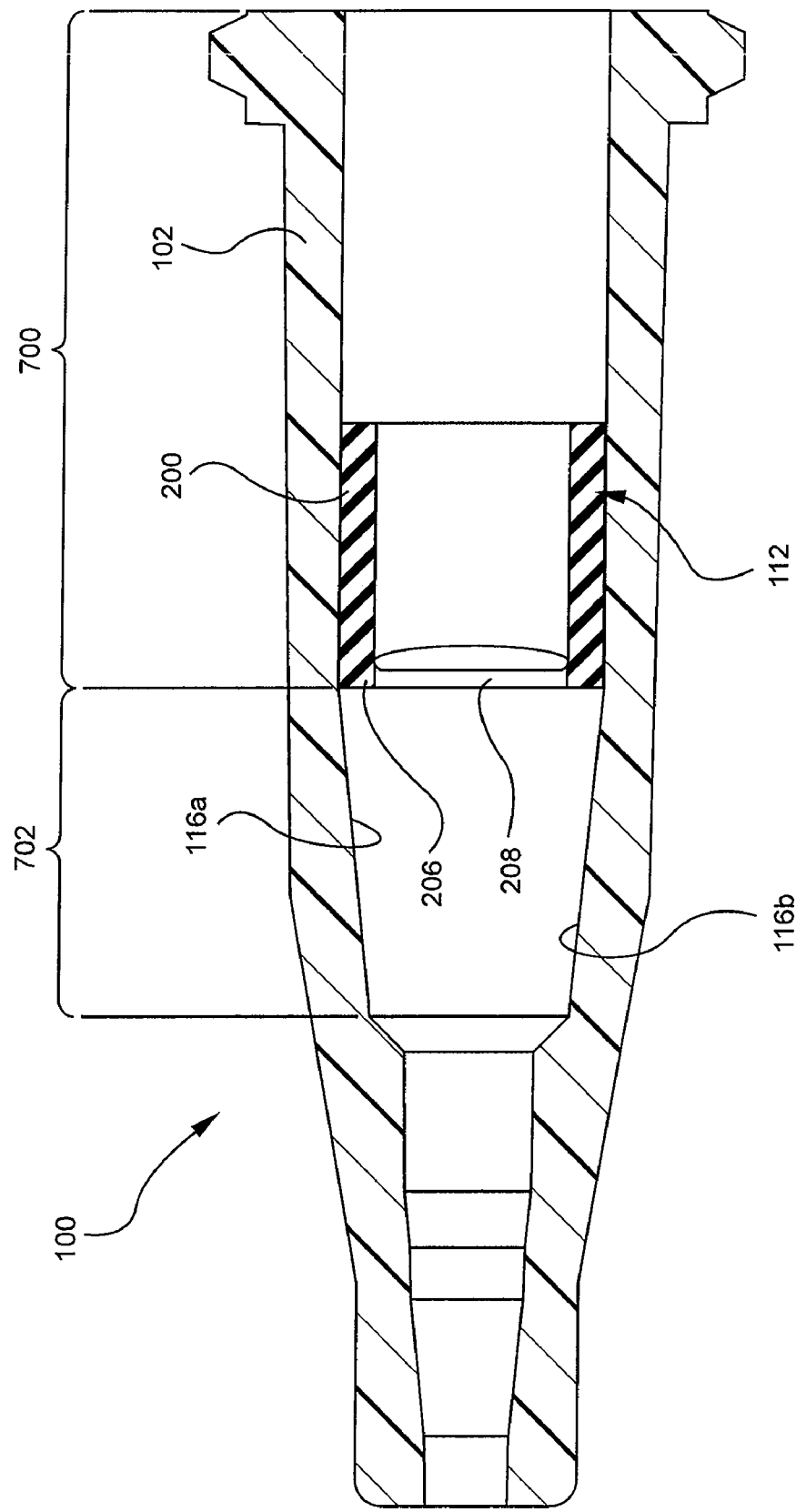
FIG. 7 is a cross-sectional view of an intravenous catheter adapter and blood control valve where the blood control valve is in an uncompressed state.

Referring now to FIG. 7, in some embodiments, the blood control valve 112 may be initially positioned to reside within a distal or intermediate portion of the hollow interior region 108 of the catheter adapter 102, where such portion has a substantially circular cross-section 700. The diameter of the substantially circular cross-section 700 may be at least slightly larger than the diameter of a substantially cylindrical blood control valve 112. Thus, the blood control valve 112 may be inserted into a distal end 106 of the catheter adapter 102 and positioned appropriately. In certain embodiments, the diameter of the catheter adapter 102 may be closely matched to that of the blood control valve 112 to limit rotation and movement of the blood control valve 112 therein. Further, proper orientation and retention of the blood control valve 112 with respect to the catheter adapter 102 may be achieved and reliably maintained by engaging the mating positioning features 212 of each.

As previously discussed, a proximal portion of the hollow interior region 108 may include compression features 116 to modify its otherwise circular cross-section 700. The compression features 116 and catheter adapter 102 may be monolithic in nature, so that the compression features 116 are molded into the hollow interior region 108. Alternatively, the compression features 116 may be independently manufactured and fitted within the hollow interior region 108 as appropriate. In any case, the compression features 116 may reduce the diameter of the hollow interior region 108 in substantially opposite radial directions, thereby defining within the hollow interior region 108 a substantially oblong or elongate cross-section 702.

Figure 8:
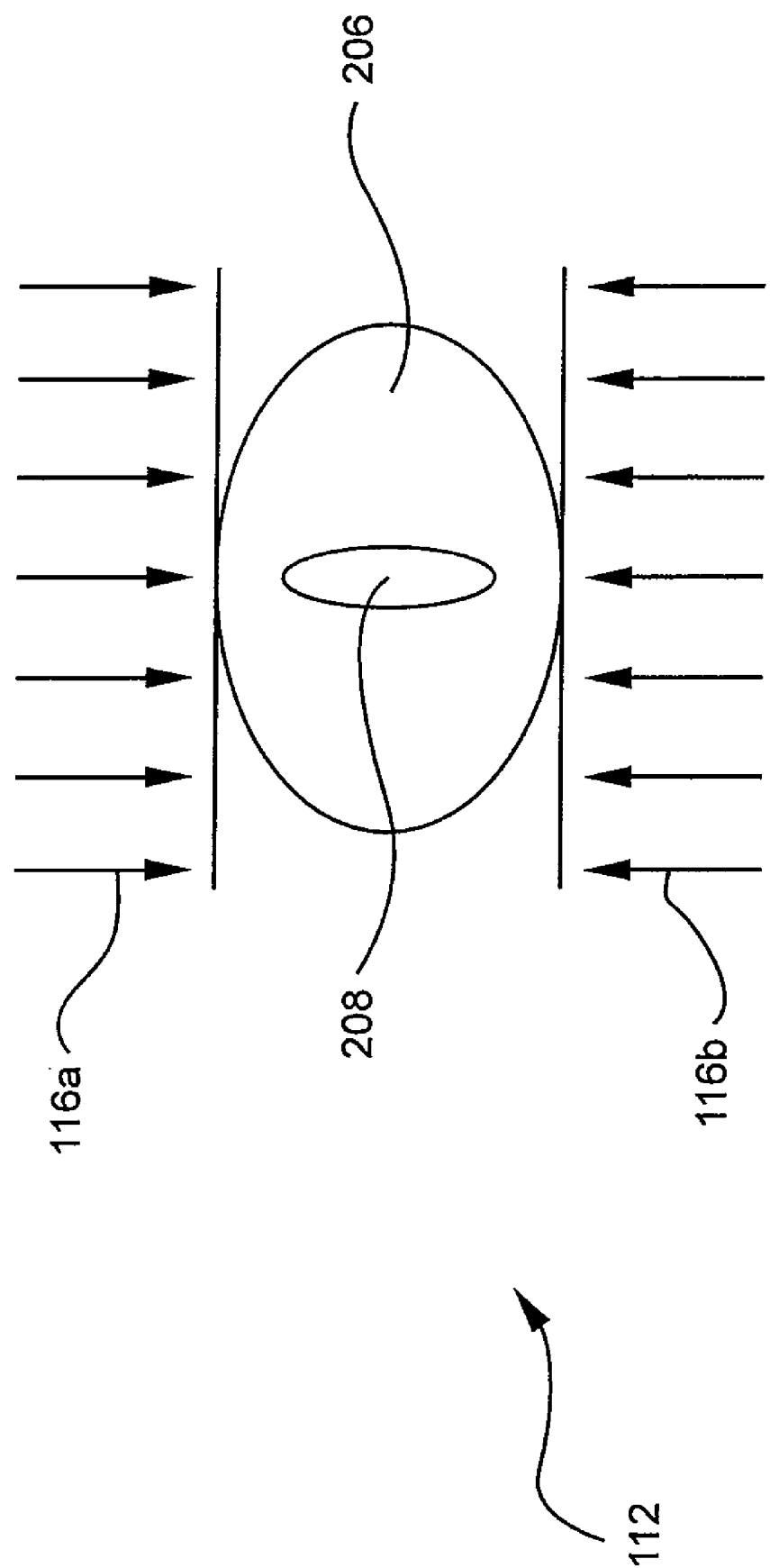
FIG. 8 is an alternate cross-sectional view of an intravenous catheter adapter and blood control valve depicting compression of the blood control valve by compression features in the intravenous catheter adapter.

Referring now to FIG. 8, the blood control valve 112 may be translated within the hollow interior region 108 in a proximal direction, such that the compression features 116 deform the otherwise cylindrical cross-section of the blood control valve 112. In certain embodiments, the blood control valve 112 may be deformed such that it assumes substantially the same cross-section as the hollow interior region 108 that surrounds it, as defined by the compression features 116.

The compression features 116 may be situated to correspond to opposite ends 224a, 224b of the slit 208. Thus, translating the blood control valve 112 within the hollow interior region 108 to a position where the compression features 116 radially deform the outer shell 200 may open the slit 208 to provide a fluid path. Specifically, such compression may force the outer shell 200 to assume a substantially oblong or elongate cross-sectional shape, thereby stretching the inner valve portion 206 across a plane perpendicular to the longitudinal axis 118 to force adjacent sides of the slit 208 in opposite radial directions.

Figure 9:
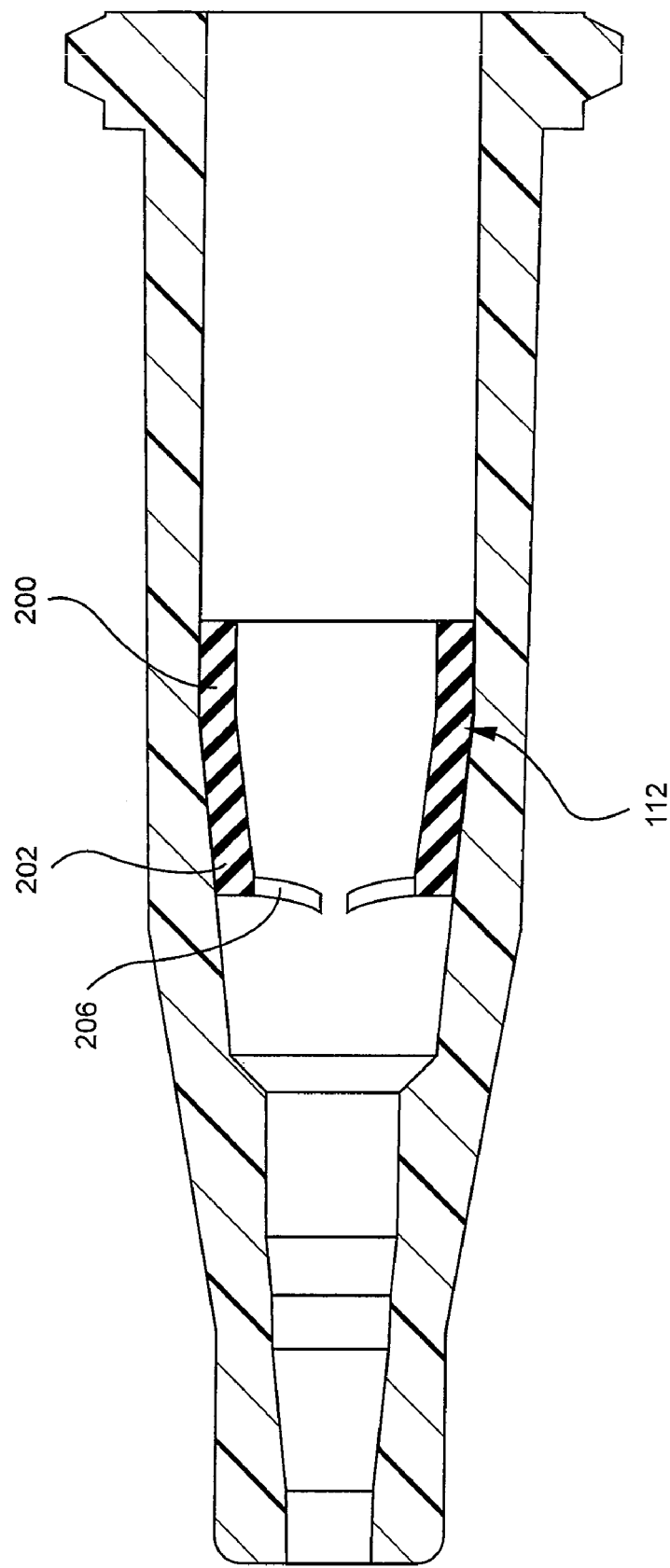
FIG. 9 is an alternate cross-sectional view of the intravenous catheter adapter and blood control valve of FIG. 8, depicting the blood control valve in a compressed state.

Referring now to FIG. 9, the oblong or elongate cross-section 702 of the hollow interior region 108 where the compression features 116 are located may cause progressive deformation of the blood control valve 112 as it is translated in a proximal direction. In some embodiments, the inner valve portion 206 may substantially correspond to a proximal end 202 of the blood control valve 112 to reduce a distance over which the blood control valve 112 must be translated to cause the slit 208 to open. Further, an inside volume of the blood control valve 112, as defined by the outer shell 200, may be substantially hollow to facilitate its easy deformation, as well as to provide a substantially unobstructed fluid path.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An apparatus to control blood flow through an intravenous catheter, the apparatus comprising:
    an intravenous catheter adapter having a hollow interior region therein, the hollow interior having a first portion and a second portion;
    a blood control valve positioned within the first portion of the hollow interior region, the blood control valve having a hollow resilient outer shell and an inner valve forming a proximal end of the hollow resilient outer shell, the inner valve further comprising a slit configured to open upon translating the blood control valve into the second portion of the hollow interior region, wherein a portion of the resilient outer shell is compressed within the second portion of the hollow interior;
    a groove formed into the outer surface of the blood control valve and aligned with the longitudinal axis of the intravenous catheter adapter to orient the blood control valve within the hollow interior region; and
    a retention feature disposed within the groove to retain the blood control valve within the hollow interior region.

2. The apparatus of claim 1, wherein at least one of the resilient outer shell and the inner valve portion comprises an elastomeric material.

3. The apparatus of claim 2, wherein the elastomeric material comprises silicone rubber.

4. The apparatus of claim 1, wherein the inner valve portion is configured to receive a needle therethrough.

5. The apparatus of claim 1, wherein the second portion of the hollow interior region further comprises a compression feature to selectively radially compress the hollow resilient outer shell to open the slit of the inner valve portion.

6. The apparatus of claim 5, wherein the blood control valve is oriented within the first portion of the hollow interior region such that a Luer device inserted into the intravenous catheter adapter translates the blood control valve in a proximal direction.

7. The apparatus of claim 6, wherein the Luer device translates the blood control valve to a position within the second portion of the hollow interior region substantially corresponding to the compression feature, wherein the compression feature radially compresses the hollow resilient outer shell to bias open the slit.

8. The apparatus of claim 1, wherein the proximal end of the blood control valve consists of a single flat surface with the slit formed therethrough.

9. The apparatus of claim 1, wherein the retention feature is disposed on a distal portion of the groove.

10. The apparatus of claim 1, wherein the groove is a first groove, the apparatus further comprising a second groove, wherein the first and second grooves are disposed on opposite halves of the blood control valve.

11. The apparatus of claim 10, wherein a first and a second compression feature of the hollow interior region contact the blood control valve one or more locations between the first and the second grooves, the first and the second compression features being on opposite sides of the interior region.

12. A method to control blood flow through an intravenous catheter, the method comprising:
    providing a blood control valve having a hollow resilient outer shell;
    closing a proximal end of the hollow resilient outer shell with an inner valve portion, wherein the inner valve portion comprises a slit configured to open upon radially compressing the hollow resilient outer shell;
    providing an intravenous catheter adapter having a hollow interior region therein, the hollow interior having a first portion and a second portion;
    positioning the blood control valve within the first portion of the hollow interior region;
    integrating a groove into at least one of the intravenous catheter adapter and the blood control valve to orient the blood control valve within the hollow interior region, the groove being aligned with the longitudinal axis of the intravenous catheter adapter;
    integrating a retaining feature within the groove to retain the blood control valve within the hollow interior region; and
    radially compressing the resilient outer shell by translating a portion of the blood control valve into the second portion of the hollow interior.

13. The method of claim 12, further comprising integrating into the second portion of the hollow interior region of the intravenous catheter adapter a compression feature to selectively radially compress the hollow resilient outer shell.

14. The method of claim 13, further comprising translating the blood control valve to a position within the second portion of the hollow interior substantially corresponding to the compression feature.

15. The method of claim 14, wherein translating the blood control valve actuates the compression feature to radially compress the hollow resilient outer shell.

16. The method of claim 13, further comprising orienting the blood control valve within the first portion of the hollow interior region such that a Luer device inserted into a distal end of the intravenous catheter adapter translates the blood control valve to a position within the second portion of the hollow interior region substantially corresponding to the compression feature.

17. The method of claim 13, further comprising inserting a Luer device into a distal end of the intravenous catheter adapter to translate the blood control valve to a position substantially corresponding to the compression feature.

18. An intravenous catheter assembly to control fluid flow through an intravenous catheter, the intravenous catheter assembly comprising:
    means for piercing a blood vessel to acquire intravenous access;
    means for mediating fluid communication between the blood vessel and an external fluid source, the means for mediating fluid communication comprising a hollow interior region having a first portion and a second portion;
    means for controlling fluid flow through the means for mediating fluid communication, the means for controlling fluid flow being positioned within the first portion of the hollow interior region and comprising hollow resilient outer shell means and inner valve means forming a proximal end of the hollow resilient outer shell means, wherein the inner valve means comprises slit means configured to open upon radially compressing the hollow resilient outer shell means by translating a portion of the means for controlling fluid flow into the second portion of the hollow interior region;

a groove aligned with the longitudinal axis of the intravenous catheter adapter and disposed on at least one of the means for piercing a blood vessel and the means for mediating fluid communication; and a retention feature disposed within the groove.

19. The intravenous catheter assembly of claim 18, wherein the second portion of the hollow interior region of the means for mediating fluid communication comprises means for radially compressing the resilient outer shell means.

20. The intravenous catheter assembly of claim 19, wherein the means for radially compressing the resilient outer shell means is actuated upon inserting a Luer device into the means for mediating fluid communication to translate a portion of the means for controlling fluid flow to a position within the second portion of the hollow interior region substantially corresponding to the means for radially compressing the hollow resilient outer shell means.

* * * * *